(12) United States Patent
Yamano

(10) Patent No.: US 9,050,577 B2
(45) Date of Patent: Jun. 9, 2015

(54) CARRIER FOR HOLDING NUCLEIC ACID

(75) Inventor: Hirofumi Yamano, Yamaguchi (JP)

(73) Assignee: Toyo Kohan Co., Ltd., Tokyo (JP)

( * ) Notice: Subject to any disclaimer, the term of this patent is extended or adjusted under 35 U.S.C. 154(b) by 396 days.

(21) Appl. No.: 13/395,137

(22) PCT Filed: Sep. 9, 2010

(86) PCT No.: PCT/JP2010/065518
§ 371 (c)(1),
(2), (4) Date: Mar. 9, 2012

(87) PCT Pub. No.: WO2011/030823
PCT Pub. Date: Mar. 17, 2011

(65) Prior Publication Data
US 2012/0171503 A1 Jul. 5, 2012

(30) Foreign Application Priority Data

Sep. 10, 2009 (JP) ................. 2009-209489

(51) Int. Cl.
*B01J 19/00* (2006.01)
*C12Q 1/68* (2006.01)

(52) U.S. Cl.
CPC .......... *B01J 19/0046* (2013.01); *C12Q 1/6837* (2013.01); *C12Q 1/6834* (2013.01); *B01J 2219/00387* (2013.01); *B01J 2219/00529* (2013.01); *B01J 2219/00596* (2013.01); *B01J 2219/00608* (2013.01); *B01J 2219/00612* (2013.01); *B01J 2219/00635* (2013.01); *B01J 2219/00637* (2013.01); *B01J 2219/00659* (2013.01); *B01J 2219/00722* (2013.01)

(58) Field of Classification Search
None
See application file for complete search history.

(56) References Cited

U.S. PATENT DOCUMENTS

2008/0188376 A1  8/2008 Ikegaya et al.

FOREIGN PATENT DOCUMENTS

| JP | 2003504595 | 2/2003 |
| JP | 2004198260 | 7/2004 |
| JP | 2008035773 | 2/2008 |
| JP | 2008141969 | 6/2008 |
| WO | WO 01/02538 | 1/2001 |

OTHER PUBLICATIONS

Machine translation of JP 2004-198260 A, Jul. 2004.*
Capecchi, Barbara, et al., "Neisseria Meningitidis NadA Is a New Invasion Which Promotes Bacterial Adhesion to and Penetration Into Human Epithelial Cells", Molecular Microbiology, 2005, vol. 55, No. 3, pp. 687-698.

* cited by examiner

*Primary Examiner* — Ramsey Zacharia
(74) *Attorney, Agent, or Firm* — McCarter & English

(57) ABSTRACT

A solid support for maintaining a uniform spot shape while improving the capacity for immobilization of nucleic acids upon spotting of nucleic acids onto a solid support is provided. A substrate has a base material, an electrostatic layer formed on the base material in order to electrostatically attract nucleic acids, and carboxyl groups formed on the electrostatic layer, wherein the ratio, (COO peak intensity)/(C—C peak intensity) in the C1s spectra obtained by X-ray photoelectron spectrometry (XPS) performed for the surface of the substrate ranges from 0.10 to 0.20. The solid support for immobilizing nucleic acids is produced by active esterification of carboxyl groups of the substrate.

10 Claims, 2 Drawing Sheets

PA concentration = polyacrylic acid concentration

CARRIER FOR HOLDING NUCLEIC ACID

RELATED APPLICATIONS

This application is a national stage application filed under 35 USC §371 of PCT/JP2010/065518, filed Sep. 9, 2010, which claims the benefit of Japanese Patent Application No. 2009-209489, filed Sep. 10, 2009, both of which are incorporated herein, in entirety, by reference.

TECHNICAL FIELD

The present invention relates to a solid support for immobilizing nucleic acids such as DNA and a method for producing the same.

BACKGROUND OF THE INVENTION

Technical development for the efficient analysis of all of the gene functions of various organisms is proceeding. Microarrays are used as analytical means this purpose. Microarrays are generally formed such that many nucleic acid fragments are aligned and immobilized on a solid support such as slide glass. Microarrays are used for methods that involve immobilizing a nucleic acid fragment sample complementary to a nucleic acid fragment (immobilized on a microarray) on a microarray via hybridization, followed by detection. As means for detecting the thus formed hybrids, a method using a fluorescent label or a radioactive label bound in advance to a nucleic acid fragment sample and a method using an intercalator that contains fluorogenic groups or conductive groups to be incorporated into hybrids are known, for example.

Examples of a method for preparing a microarray include a method (referred to as "on-chip method") that involves directly synthesizing nucleic acids on a solid support surface and a method that involves immobilizing previously prepared nucleic acid fragments on a solid support surface. The former on-chip method involves performing a combination reaction (combinatorial synthesis) on many fine matrices on a solid support using protecting groups to be selectively removed by light irradiation and a photolithography technique and a solid phase synthesis technique to be used for semiconductor production, thereby achieving the simultaneous synthesis of many types of nucleic acid.

Meanwhile, the latter method involves spotting a previously prepared nucleic acid fragment sample or the like on a solid support surface and then binding and immobilizing the sample using covalent bonds or ionic bonds. Examples of such a method include a method that involves spotting a nucleic acid fragment sample on a solid support surface treated with a polycation (e.g., polylysine and polyethylene imine) with the use of a spotter provided with a microarray preparation apparatus, and then electrostatically binding and immobilizing the nucleic acid sample to the solid support using the electric charge of the sample; a method that involves synthesizing nucleic acids into which reaction active groups have been introduced in advance, spotting them on a surface-treated solid support surface using a spotter, and then immobilizing them via covalent bonds; and a method that involves introducing reaction active groups such as active ester groups that form covalent bonds with nucleic acids onto a solid support surface, and then immobilizing the nucleic acids via covalent bonds. Also, a method is known that involves electrostatically attracting nucleic acids to a solid support surface comprising a substrate, an electrostatic layer formed on the substrate for electrostatically attracting nucleic acids, and functional groups capable of covalently binding with the nucleic acids formed on the electrostatic layer, and then immobilizing the nucleic acids via covalent bonds (patent document 1) (JP Patent Publication (Kokai) No. 2008-292482 A).

Various spotters employing a pin system by which a pin tip is mechanically brought into contact with a solid support surface; an ink-jet system based on the principle of an inkjet printer; or the like are used for immobilizing nucleic acids on a solid support surface to form many spots. Most of the thus immobilized spots vary in shape. For example, spots may be falcated, doughnut-shaped, or spilled out. Varied spot shapes lead to varied signal intensities, resulting in data with low reliability. Therefore, to improve the analytical accuracy of microarrays, firm immobilization of nucleic acids in spots formed on a solid support surface, spot shapes and spot sizes that are as uniform as possible, and good reproducibility are desired when any apparatus is used.

SUMMARY OF THE INVENTION

Object to be Achieved by the Invention

An object of the present invention is to provide a solid support for maintaining a uniform spot shape while improving the capacity to immobilize nucleic acids upon spotting of nucleic acids onto a solid support.

Means for Solving the Problem

The present inventors have found that upon production of a solid support having active ester groups on an electrostatic layer and specifically upon introduction of carboxyl groups onto a base material having an electrostatic layer, a uniform spot shape can be maintained while improving the capacity to immobilize nucleic acids by adjusting the carboxyl group amount, which is measured as the ratio of COO peak intensity to C—C peak intensity for the C1s spectrum obtained by X-ray photoelectron spectrometry (XPS), to an appropriate level.

Specifically, the present invention encompasses the following (1) to (13).
(1) A solid support for immobilizing a nucleic acid, which is prepared by active esterification of a carboxyl group of a substrate that comprises a base material, an electrostatic layer formed on the base material capable of electrostatically attracting a nucleic acid, and a carboxyl group formed on the electrostatic layer, wherein the ratio, (COO peak intensity)/(C—C peak intensity), in the C1s spectra obtained by X-ray photoelectron spectrometry (XPS) performed upon the surface of the substrate ranges from 0.10 to 0.20.
(2) The solid support according to (1), which has a N-hydroxysuccinimide group that is formed by active esterification of a carboxyl group.
(3) The solid support according to (1) or (2), wherein the electrostatic layer is formed by plasma-treating the base material in an ammonia gas atmosphere.
(4) The solid support according to any one of (1) to (3), wherein the base material comprises a carbon layer on its surface and an electrostatic layer has been formed on the carbon layer.
(5) A solid support for immobilizing a nucleic acid, which is obtained by treating a base material with an amino-group-containing compound so as to form an electrostatic layer for electrostatically attracting a nucleic acid, bringing a polyvalent carboxylic acid solution with a concentration ranging from 10 g/l to 70 g/l into contact with the electrostatic layer so as to introduce a carboxyl group, and then activating the carboxyl group to form an active ester group.

(6) The solid support according to (5), wherein the active ester group is an N-hydroxysuccinimide group.

(7) The solid support according to (5) or (6), wherein the polyvalent carboxylic acid is polyacrylic acid.

(8) The solid support according to any one of (5) to (7), wherein the base material is plasma-treated in an ammonia gas atmosphere, so as to form the electrostatic layer.

(9) A solid support on which a nucleic acid is immobilized, which is prepared by immobilizing a nucleic acid on the solid support according to any one of (1) to (8).

(10) A method for producing a solid support for immobilizing a nucleic acid, comprising the steps of:

treating a base material with an amino-group-containing compound so as to form an electrostatic layer for electrostatically attracting a nucleic acid;

bringing a polyvalent carboxylic acid solution with a concentration ranging from 10 g/l to 70 g/l into contact with the electrostatic layer so as to introduce a carboxyl group; and activating the carboxyl group so as to form an active ester group.

(11) The method according to (10), wherein the active ester group is an N-hydroxysuccinimide group.

(12) The method according to (10) or (11), wherein the polyvalent carboxylic acid is polyacrylic acid.

(13) The method according to any one of (10) to (12), wherein the base material is plasma-treated in an ammonia gas atmosphere so as to form an electrostatic layer.

This description includes part or all of the contents as disclosed in the description and/or drawings of Japanese Patent Application No. 2009-209489, which is a priority document of the present application.

Effect of the Invention

The present invention makes it possible to maintain uniform spot shape while improving the capacity to immobilize nucleic acids upon spotting of nucleic acids onto a solid support. Also, a solid support with good appearance can be obtained. As a result, the analytical accuracy of the microarray can be improved.

DETAILED DESCRIPTION OF THE INVENTION

Figure 1:
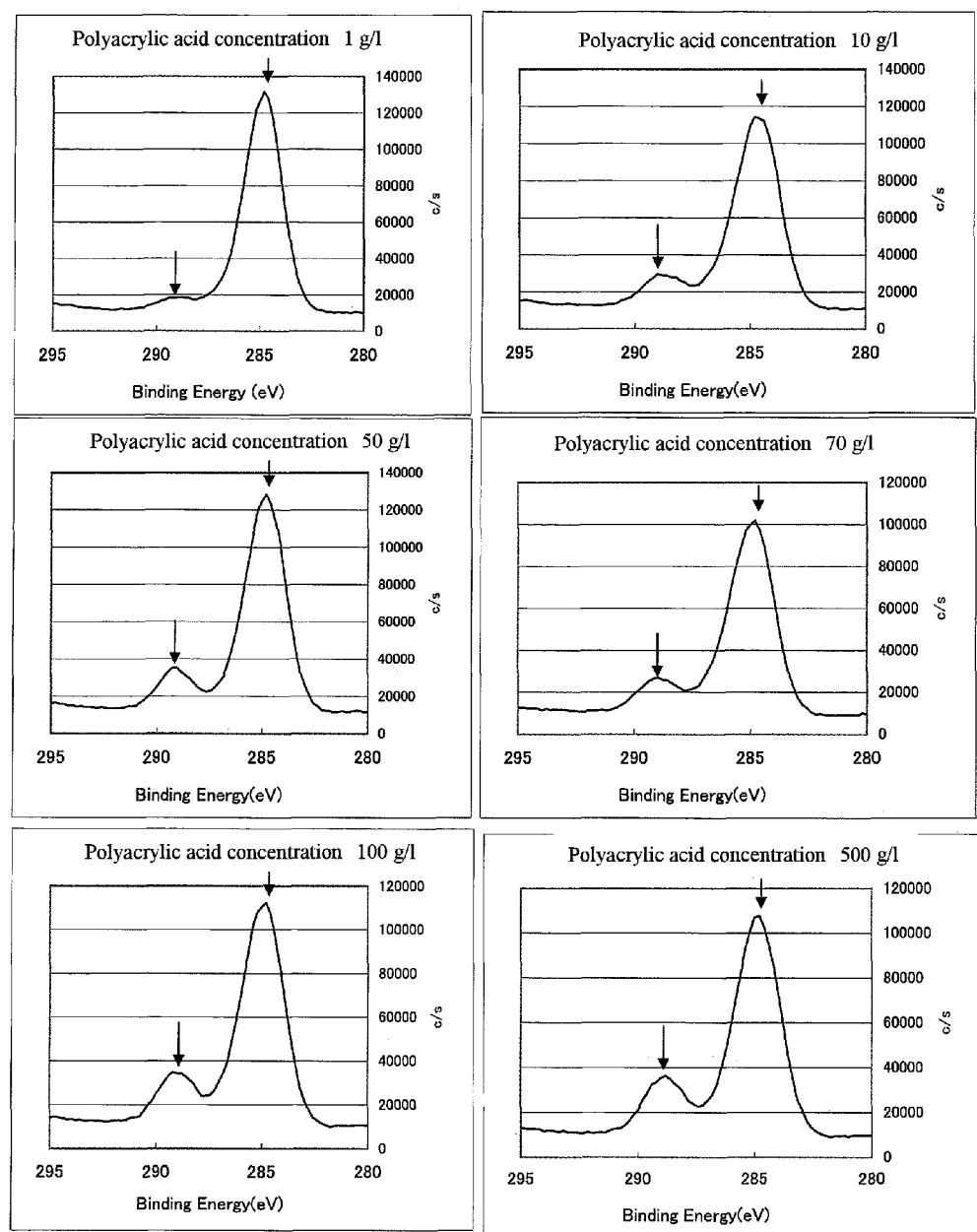
FIG. 1 shows the charts of C1s spectra obtained by measuring substrates into which carboxyl groups were introduced with the use of an X-ray photoelectron spectrometer.

As base materials to be used in the present invention, materials known in the art can be used and are not particularly limited. Examples of such materials include: noble metals such as platinum, platinum black, gold, palladium, rhodium, silver, mercury, tungsten, and compounds thereof; conductive materials such as graphite and carbon represented by carbon fiber; silicon materials represented by single crystal silicon, amorphous silicon, silicon carbide, silicon oxide, and silicon nitride, as well as composite materials of such silicon materials, represented by SOI (silicon on insulator) and the like; inorganic materials such as glass, quartz glass, borosilicate glass, alumina, sapphire, ceramics, forsterite, and photosensitive glass; and organic materials such as polyethylene, ethylene, polypropylene, cyclic polyolefin, polyisobutylene, polyethylene terephthalate, unsaturated polyester, fluorine-containing resin, polyvinyl chloride, polyvinylidene chloride, polyacetic acid vinyl, polyvinyl alcohol, polyvinyl acetal, acryl resin, polyacrylonitrile, polystyrene, acetal resin, polycarbonate, polyamide, phenol resin, urea resin, epoxy resin, melamine resin, styrene-acrylonitrile copolymer, acrylonitrile-butadienestyrene copolymer, polyphenylene oxide, and polysulfone. The shape of a base material is also not particularly limited, and is preferably planar.

When the solid support of the present invention is used for a microarray, in view of integration, a base material having a fine planar structure, such as a planar base material that is 2 mm to 5 mm square, is preferably used. Furthermore, a base material made of a silicon material or a resin material is preferably used, since a fine planar structure can be easily produced. In particular, a base material comprising single crystal silicon is more preferably used. Examples of such single crystal silicon include single crystal silicon in which the orientation of the crystallographic axis is slightly and partially varied (which may also be referred to as "mosaic crystal") and single crystal silicon containing atomic scale disorders (lattice defects).

A base material comprising a carbon layer on its surface is preferably used. Formation of a carbon layer enables firm immobilization of an electrostatic layer and carboxyl groups on the base material. Examples of carbon layers that are preferably used herein include, but are not particularly limited to, surfaces of synthetic diamond, high pressure synthetic diamond, natural diamond, soft diamond, amorphous carbon, or carbonaceous matter (e.g., graphite, fullerene, and carbon nanotubes), mixtures thereof, or laminated products thereof. Also, carbides such as a hafnium carbide, a niobium carbide, a silicon carbide, a tantalum carbide, a thorium carbide, a titanium carbide, an uranium carbide, a tungsten carbide, a zirconium carbide, a molybdenum carbide, a chrome carbide, and a vanadium carbide can also be used. Here the term "soft diamond" is a generic name used for incomplete diamond structures that are mixtures of diamond and carbon, such as Diamond Like Carbon (DLC), and the mixture fractions thereof are not particularly limited. A carbon layer is excellent in chemical stability and is advantageous in that it can withstand the subsequent introduction of an electrostatic layer or carboxyl groups as well as reaction upon binding of nucleic acids. A carbon layer is also advantageous in that its binding reaction with nucleic acids results in a low degree of non-specific adsorption. A base material itself comprising a carbon layer can also be used herein.

In the present invention, a carbon layer can be formed by a known method. Examples of such a method include a microwave plasma CVD (chemical vapor deposit) method, an ECRCVD (electric cyclotron resonance chemical vapor deposit) method, an ICP (inductive coupled plasma) method, a direct current sputtering method, an ECR (electric cyclotron resonance) sputtering method, an ionized evaporation method, an arc evaporation method, a laser evaporation method, an EB (electron beam) evaporation method, and a resistance heating evaporation method. The thickness of the carbon layer preferably ranges from 1 nm to 100 µm.

Also, a monolayer of Ti, Au, Pt, Nb, Cr, TiC, TiN, or the like or a composite membrane thereof may be produced as a reflective layer on the surface or the rear surface of a base material. The thickness of the reflective layer is required to be entirely uniform, so that it is preferably 10 nm or more, and is further preferably 100 nm or more.

When glass is used as a base material, the surface is preferably purposefully subjected to surface roughening with Ra (JIS B 0601) ranging from 1 nm to 1000 nm. Such surface roughening is convenient in that the surface area of the base material increases and large amounts of nucleic acids can be immobilized at high density.

An electrostatic layer is formed on the base material in order to electrostatically attract nucleic acids. Such an electrostatic layer is not particularly limited, as long as it can electrostatically attract nucleic acids, so as to increase the amount of nucleic acids immobilized. For example, such an electrostatic layer can be formed using a compound having positive electric charge such as an amino-group-containing compound.

Examples of the amino-group-containing compound include compounds in which an unsubstituted amino group ($-NH_2$) or an amino group ($-NHR$; R denotes a substituent) has been substituted with a $C_{1-6}$ alkyl group or the like, such as ammonia, ethylenediamine, hexamethylenediamine, n-propylamine, monomethylamine, dimethylamine, monoethylamine, diethylamine, allylamine, aminoazobenzene, aminoalcohol (e.g., ethanolamine), acrinol, aminobenzoic acid, aminoantraquinone, an amino acid (glycine, alanine, valine, leucine, serine, threonine, cysteine, methionine, phenylalanine, tryptophan, tyrosine, proline, cystine, glutamic acid, aspartic acid, glutamine, asparagine, lysine, arginine, or histidine), aniline, or a polymer thereof (e.g., polyallylamine or polylysine) or a copolymer thereof; or 4,4',4''-triaminotriphenyl methane, triamterene, spermidine, spermin, putrescine, or a polyamine (polyvalent amine) such as polyallylamine.

An electrostatic layer can be formed by plasma-treating a base material in an ammonia gas atmosphere, for example. Alternatively, an amino-group-containing compound (e.g., an ammonia gas) may be introduced into a film (membrane)-forming apparatus upon production of a carbon layer, so that an electrostatic layer can be formed as a carbon-based film (membrane) containing amino groups.

Carboxyl groups may be introduced after evaporation of an amino-group-containing compound and a carbon compound onto a base material in order to increase affinity (that is, adhesion between an electrostatic layer and a base material). A carbon compound to be used herein is not particularly limited, as long as it can be supplied as a gas. For example, methane, ethane, and propane, which are gases at ordinary temperatures, are preferred. As an evaporation method, an ionized evaporation method is preferred. Regarding conditions of the ionized evaporation method, working pressure preferably ranges from 0.1 Pa to 50 Pa and acceleration voltage preferably ranges from 200 V to 1000 V.

An electrostatic layer may also be formed by chlorinating the surface of a base material through ultraviolet irradiation in a chlorine gas, causing a polyvalent amine (e.g., polyallylamine, polylysine, 4,4',4''-triaminotriphenyl methane, or triamterene) selected from among amino-group-containing compounds to react, and then introducing amino groups to the ends on sides that do not bind with the base material.

When a reaction for introducing carboxyl groups onto an electrostatic layer (e.g., introduction of carboxyl groups using dicarboxylic acid or polyvalent carboxylic acid) is performed in a solution, carboxyl groups are preferably introduced after the formation of the electrostatic layer. Examples of a solvent for the above solution include water, N-methylpyrrolidone, ethanol, and a mixture thereof.

An electrostatic layer can also be formed by immersing a base material in a solution containing an amino-group-containing compound. In such case, the use of a polyvalent amine, and particularly polyallylamine, as an amino-group-containing compound results in good adhesion with the base material and an improved amount of nucleic acids immobilized.

The thickness of an electrostatic layer preferably ranges from 1 nm to 500 μm.

As described above, a substrate is prepared by introducing carboxyl groups onto the electrostatic layer formed on the surface of the base material. Examples of a compound to be used for introduction of carboxyl groups include: halo carboxylic acid represented by the formula: $X-R^1-COOH$ (wherein X denotes a halogen atom and $R^1$ denotes a $C_{1-12}$ divalent hydrocarbon group), such as chloroacetic acid, fluoroacetic acid, bromoacetic acid, iodoacetic acid, 2-chloropropionic acid, 3-chloropropionic acid, 3-chloroacrylic acid, and 4-chlorobenzoic acid; dicarboxylic acid represented by the formula: $HOOC-R^2-COOH$ (wherein $R^2$ denotes a single bond or $C_{1-12}$ divalent hydrocarbon group), such as oxalic acid, malonic acid, succinic acid, maleic acid, fumaric acid, and phthalic acid; polyvalent carboxylic acid such as polyacrylic acid, polymethacrylic acid, trimellitic acid, and butane tetracarboxylic acid; keto acid or aldehyde acid represented by the formula: $R^3-CO-R^4-COOH$ (wherein $R^3$ denotes a hydrogen atom or $C_{1-12}$ divalent hydrocarbon group and $R^4$ denotes a $C_{1-12}$ divalent hydrocarbon group); monohalides of dicarboxylic acid represented by the formula: $X-OC-R^5-COOH$ (wherein X denotes a halogen atom and $R^5$ denotes a single bond or $C_{1-12}$ divalent hydrocarbon group), such as succinic acid monochloride and malonic acid monochloride; and acid anhydrides such as anhydrous phthalic acid, anhydrous succinic acid, anhydrous oxalic acid, anhydrous maleic acid, and anhydrous butane tetracarboxylic acid. Preferably, polyvalent carboxylic acid and more preferably, polyacrylic acid are used. When polyvalent carboxylic acid is used, carboxyl groups and amino groups of the electrostatic layer are condensed to form amide bonds, so that carboxyl groups can be introduced via firm binding. Also, polyvalent carboxylic acid such as polyacrylic acid, polymethacrylic acid, trimellitic acid, or butanetetracarboxylic acid has the effect of improving hydrophilicity.

Carboxyl groups can be introduced by bringing a base material with an electrostatic layer into contact with a solution of the above compound, preferably polyvalent carboxylic acid and more preferably polyacrylic acid. As a solvent for such a solution, an organic solvent such as water or alcohol can be used. For example, ethanol, IPA, methanol, N,N-dimethylformamide, acetone, dioxane, alcohol, or a mixture thereof can be used herein.

The thus obtained substrate, with an electrostatic layer onto which carboxyl groups have been introduced is characterized in that: the ratio of COO peak intensity to C—C peak intensity for the C1s spectra obtained by analysis of the chemical binding state of carbons using X-ray photoelectron spectrometry (XPS) ranges from 0.10:1 to 0.20:1, and preferably ranges from 0.12:1 to 0.18:1. The intensity ratio is expressed by the ratio of the peak intensity (COO peak intensity) derived from carboxyl groups (COO(H) bond), for which bound energy appears at 288.8 eV (peak top), to the peak intensity (C—C peak intensity) derived from C—C bonds, for which bound energy appears at 284.7 eV (peak top), in the C1s spectra (the horizontal axis indicates bound energy and the vertical axis indicates energy intensity) measured by X-ray photoelectron spectrometry.

Through adjustment of the carboxyl group amount so as to satisfy the required conditions, a uniform spot shape can be maintained while improving capacity for immobilization of nucleic acids (good signal intensity can be obtained upon detection of nucleic acids) on a solid support after activation of carboxyl groups. Also, stain formation on a solid support can be prevented, so that a good appearance can be obtained.

The carboxyl group amount can be appropriately adjusted based on a method for introducing carboxyl groups, so as to obtain the above peak intensity ratio. For example, when a base material having an electrostatic layer is brought into contact with a solution of a compound to be used for the introduction of carboxyl groups, the carboxyl group amount can be adjusted by adjusting the concentration of the compound in the solution. When a solution of polyvalent carboxylic acid, and more preferably polyacrylic acid, is used, a polyvalent carboxylic acid solution with a concentration ranging from 10 g/l to 70 g/l, and preferably ranging from 10 g/l to 35 g/l, is used, so that the peak intensity ratio can be adjusted to the above ratio, (COO peak intensity)/(C—C peak intensity) in the C1s spectra obtained by X-ray photoelectron spectrometry (XPS).

The solid support of the present invention can be obtained by activating carboxyl groups introduced as described above to result in active ester groups (active esterification). The term "active ester group" refers to an ester group having an electron-withdrawing group with high acidity on the alcohol side of the ester group and activating a nucleophilic reaction. Such an active ester group specifically refers to an ester group with a high degree of reaction activity. Moreover, such an active ester group has an electron-withdrawing group on the alcohol side of the ester group, which is activated to a degree higher than alkyl ester. Such an active ester group has reactivity to groups such as amino groups, thiol groups, and hydroxyl groups. More specifically, phenol esters, thiophenol esters, N-hydroxyamine esters, cyanomethyl esters, esters of heterocyclic hydroxy compounds, and the like are known as active ester groups displaying a much higher degree of activity than alkyl esters and the like. More specifically, examples of such active ester groups include p-nitro phenyl groups, N-hydroxysuccinimide groups, succinimide groups, phthalic imide groups, and 5-norbornene-2,3-dicarboxyimide groups. In particular, an N-hydroxysuccinimide group is preferably used for immobilization of nucleic acids.

Active ester groups can be introduced by performing active esterification of the above-introduced carboxyl groups using a dehydrating and condensing agent such as a cyanamide and a carbodiimide (e.g., 1-[3-(dimethylamino)propyl]-3-ethyl carbodiimide) and a compound such as N-hydroxysuccinimide. As a result of this treatment, a group can be formed wherein an active ester group such as an N-hydroxysuccinimide group binds to an end of a hydrocarbon group via an amide bond (JP Patent Publication (Kokai) No. 2001-139532).

Any nucleic acid (either DNA or RNA) can be immobilized on the solid support of the present invention. In general, a nucleic acid of 1-200 nucleoteides, or preferably 5-150 nucletides is immobilized. Either single-stranded or double-stranded DNA can be immobilized.

Examples of nucleic acids in the present invention include artificial nucleic acids. Examples of artificial nucleic acids include a nucleic acid derivative resulting from conversion of diester phosphate bonds to phosphorothioate bonds in a nucleic acid, a nucleic acid derivative resulting from conversion of diester phosphate bonds to N3'—P5' phosphoamidite bonds in a nucleic acid, a nucleic acid derivative resulting from conversion of ribose-to-diester phosphate bonds to peptide-nucleic acid bonds in a nucleic acid, a nucleic acid derivative resulting from substitution of uracil in a nucleic acid with C-5 propynyluracil, a nucleic acid derivative resulting from substitution of uracil in a nucleic acid with C-5 thiazole uracil, a nucleic acid derivative resulting from substitution of cytosine in a nucleic acid with C-5 propynyl cytosine, a nucleic acid derivative resulting from substitution of cytosine in a nucleic acid with phenoxazine-modified cytosine, a nucleic acid derivative resulting from substitution of ribose in a nucleic acid with 2'-O-propyl ribose, a nucleic acid derivative resulting from substitution of ribose in a nucleic acid with 2'-O-methoxyribose, and a nucleic acid derivative resulting from substitution of ribose in a nucleic acid with 2'-methoxyethoxy ribose.

A method for immobilizing nucleic acids onto the solid support of the present invention is not particularly limited. For example, a solution is prepared by dissolving nucleic acids in a buffer, the nucleic acid solution is spotted on the solid support using a spotter apparatus, baking is performed for a predetermined time period in a heated oven, and then non-immobilized nucleic acids are removed by washing. With the use of such a spotter apparatus, many types of nucleic acid can be immobilized at different positions on the solid support, so that many tests can be conducted at once.

A nucleic-acid-immobilized solid support comprising nucleic acids immobilized on the solid support of the present invention is used for monitoring of gene expression, determination of nucleotide sequences, mutation analysis, and polymorphism analysis, for example. Hereinafter, a method for detecting a nucleic acid sample using the solid support of the present invention is as described below. First, a labeled nucleic acid sample is prepared. As a nucleic acid sample (target nucleic acid), DNA or RNA with an unknown sequence or unknown functions is generally used.

Such a labeled nucleic acid sample is generally obtained as follows, for the purpose of examining gene expression. In the case of an eukaryote, mRNA is extracted from cells or a tissue sample, and then cDNA is prepared while causing incorporation of labeled dNTP via a reverse transcription reaction. In the case of a prokaryote such as a bacterium, total RNA is extracted, since selective extraction of mRNA is difficult. When a genome is used as a sample, it can be isolated from any tissue sample except for erythrocyte samples. Examples of such a non-erythrocyte tissue sample include samples of peripheral blood lymphocytes, skin, hair, and seminal fluid. The amount of mRNA required for single hybridization differs depending on liquid level or labeling method, and it is generally several µg or less. In addition, there is a method in which mRNA is used as antisense RNA. As labeled dNTP, labeled dCTP is preferably used in view of chemical stability. Also, when nucleic acids as probes immobilized on a solid support are oligonucleotides, a nucleic acid sample is desirably prepared to have lower molecular weight.

For the purpose of examining gene mutations or polymorphisms, a labeled nucleic acid sample is generally obtained by performing PCR for a target region using a reaction system containing labeled primers or labeled dNTP.

As labels, RI labels and non-RI labels (e.g., for a fluorescence method, a biotin method, and a chemiluminescence method) are known. Fluorescent labels are preferably used. Examples of fluorescent labels include, CyDye such as Cy3 and Cy5, FITC, RITC, rhodamine, Texas Red, TET, TAMRA, FAM, HEX, and ROX. Examples of radioactivity labels include α-32P, γ-32P, and 35S.

Subsequently, the above-labeled nucleic acid sample is dissolved or dispersed in an aqueous medium such as SSC, and thus an aqueous solution of the sample is prepared. The aqueous solution is brought into contact with a solid support on which nucleic acids are immobilized, incubation is performed, and then hybridization is performed. Incubation is preferably performed at a temperature ranging from room temperature to 100° C. for 1 to 24 hours. Thus, probe nucleic acids on the solid support and nucleic acids having nucleotide sequences complementary to the probe nucleic acids form hybrids.

After completion of hybridization, washing is performed using a mixed solution of a surfactant (solution) and a buffer, and then unreacted nucleic acid samples are preferably removed. As a surfactant, sodium dodecyl sulfate is used preferably. As a buffer, a citrate buffer, a phosphate buffer, a borate buffer, a tris buffer, Good's buffer, or the like can be used, and a citrate buffer is preferably used.

Next, fluorescence signals from hybrids formed on a solid support are detected using a detector. As a detector, a fluorescence laser microscope, a cooled CCD camera, or a fluorescence scanning apparatus to which a computer is connected is used, for example. Thus, fluorescence intensity on the solid support can be automatically measured. A confocal or nonfocal laser may be used instead of a CCD camera. Thus, image data can be obtained. From the thus obtained data, target nucleic acids complementary to probe nucleic acids immobilized on a solid support can be identified. This makes it possible to produce gene expression profiles based on the results or to determine the nucleotide sequence of the nucleic acid sample. Furthermore, with the use of data analysis software or external database, more complicated forms of analysis, such as analysis of gene mutation or gene polymorphism analysis, can be performed. Alternatively, a plurality of types of nucleic acid sample labeled with different fluorescent substances are prepared. These samples are used simultaneously, so that expression levels can be compared and quantitative determination can be performed on a single solid support.

The solid support of the present invention can also be used for extension reactions of nucleic acids such as DNA. In such cases, first, primers are immobilized on the solid support, and then single-stranded or double-stranded DNA is hybridized. Thereafter, DNA complementary to DNA hybridizing to the primers is extended by a DNA extension reaction. As a primer, a single-stranded or double-stranded nucleic acid having a known length and sequence is used. The length thereof is not particularly limited. It preferably ranges from 5 to 200 nucleotides and further preferably ranges from 10 to 100 nucleotides. With the use of a conventional solid support, primers may be detached from the surface by heat treatment in an extension reaction. With the use of the solid support of the present invention, primers are not detached from the surface even when heat is applied, and an extension reaction can proceed using primers immobilized on the solid support.

During an extension reaction, labeled nucleic acids are incorporated. After an extension reaction, signals from the labels are read, so that whether or not specific DNA hybridizes to primers so as to allow an extension reaction to proceed can be detected. Accordingly, whether or not a tested sample contains DNA capable of hybridizing to the primers on the solid support can be determined. This can be a useful detection means for research and medicine. The same applies to labeling and detection.

The solid support of the present invention can also be used for nucleic acid amplification reactions. When amplification is performed by PCR, for example, first, a forward primer is immobilized on the solid support, single-stranded or double-stranded DNA is caused to hybridize thereto, and then complementary strand DNA is extended by an enzyme reaction. Furthermore, steps of 1) annealing, 2) hybridization, and 3) extension reaction are performed sequentially, so that PCR proceeds. A conventional solid support is problematic in that primers are detached by heat treatment during PCR and sufficient thermal cycle control cannot be achieved. However, with the use of the solid support of the present invention, primers remain undetached even when heat is applied. Furthermore, since the reaction is not performed in a container but rather with DNA immobilized on a solid support, the temperature can be precisely controlled during PCR, the accuracy with which the sequence of a nucleic acid is amplified is unlikely affected, non-target DNA is unlikely to be replicated, and DNA can be efficiently amplified.

Furthermore, detection with the use of the above labeled nucleic acids and amplification by PCR may be combined. As a result, even when a sample contains only a small amount of DNA capable of hybridizing to the primers on the solid support, DNA is replicated as described above, a large amount of DNA hybridizes to primers on the solid support, and the complementary strands are extended, making it possible to increase detection sensitivity.

Alternatively, strand-displacement-type DNA polymerase is selected as an enzyme to be used for an extension reaction, and then a reverse primer is added, so that DNA can be amplified on the solid support at a fixed temperature without any thermal cycle. The term "strand-displacement-type DNA polymerase" refers to DNA synthase capable of continuously resulting in complementary strand synthesis during dissociation of strands when a double-stranded region is present in the extension direction during the process of synthesis of a DNA strand complementary to template DNA. Examples of such strand-displacement-type DNA polymerase include, but are not particularly limited to, BcaBEST DNA polymerase (Takara Bio Inc.) and Phi29 DNA Polymerase (GE Healthcare Bio-Sciences KK (formerly Amersham Biosciences K.K.)).

cDNA synthesized from mRNA is subjected to the above embodiment, and thus RNA can also be subjected to the same. In this case, cDNA is obtained from mRNA using reverse transcription reaction, and cDNA can be immobilized on a solid support simultaneously with the obtainment thereof. First, reverse transcription primers are bound to active ester groups of a solid support. As primers, in general, oligo dT primers, primers complementary to specific nucleotide sequences, or random 6-nucleotide primers are used. In particular, an oligo dT primer comprising a sequence of about 10 to 20 Ts (thymine bases) corresponding to the 5'-end poly(A)$^+$ sequence of RNA is used desirably. When such an oligo dT primer is used, the 5'-end poly(A) portion of RNA serving as a template is annealed. Reverse transcriptase is caused to act on the resultant and sequential polymerization of dNTP complementary to the template RNA to the 3' end of the primer is performed, so that cDNA is synthesized in the 5' to 3' direction. Primer binding in the reverse transcription reaction, annealing, and complementary strand polymerization with reverse transcriptase can be performed under temperature control (thermal cycle) according to a conventional method. Since both reverse transcription reaction and immobilization on a solid support can be performed as described above, RT-PCR can be efficiently performed according to the method of the present invention, and the method is useful for determining quantities of mRNA.

Hereafter, the present invention is described in greater detail with reference to the examples, although the present invention is not limited thereto.

Examples

A 2.5-inch silicon wafer (SINYO CO., LTD, n Type) was subjected to dicing to result in 3 mm×3 mm (3-mm square) chips. Film formation of two DLC layers was performed on the thus obtained silicon base material using an ionized evaporation method under the following conditions.

TABLE 1

|  |  | 1st layer | 2nd layer |  |
|---|---|---|---|---|
| Raw material gas | CH₄ | 4.75 | 47.5 | (sscm) |
|  | H₂ | 0.25 | 2.5 | (sscm) |
| Working pressure |  | 3.0 | 8.0 | (Pa) |
| Substrate bias | Direct-current voltage | 500 | 500 | (V) |
|  | High-frequency output | 100 | — | (W) |
| Anode voltage |  | 50 | 50 | (V) |
| Filament | Voltage | 7 | 7 | (V) |
|  | Current | 22 | 22 | (A) |

The thus obtained silicon base material having DLC layers on its surface was subjected to plasma treatment in an ammonia gas atmosphere under the following conditions, so that amino groups were introduced.

TABLE 2

| Raw material gas | NH₃ | 30 | (sscm) |
|---|---|---|---|
| Working pressure |  | 8.0 | (sscm) |
| Substrate bias | Direct-current voltage | 500 | (Pa) |
|  | High-frequency output | — | (W) |
| Anode voltage |  | 50 | (V) |
| Filament | Voltage | 7 | (V) |
|  | Current | 22 | (A) |

The base material into which amino groups had been introduced was immersed (10 minutes×room temperature) in an aqueous polyacrylic acid solution (concentration of 1, 10, 50, 70, 100 or 500 g/l), washed with pure water, and then spray-dried with N₂ gas. In addition, in this example, an aqueous polyacrylic acid solution (25% by weight, Wako Pure Chemical Industries, Ltd.) was diluted with water to the above concentration and then used. The substrate onto which carboxyl groups had been introduced was measured using an X-ray photoelectron spectrometer (ULVAC-PHI, Inc., ESCA5100; X-ray source: Mg; areas of analysis: φ3 mm), so that C1s spectra were obtained. FIG. 1 shows the thus obtained charts. Then the ratio of the peak intensity derived from carboxyl groups (COO(H) bond), for which bound energy appeared at 288.8 eV, to the peak intensity derived from C—C bonds, for which bound energy appeared at 284.7 eV, was calculated.

Subsequently, portions for which ESCA measurement had not been performed were immersed for 30 minutes in an activator solution prepared by dissolving 0.1 M 1-[3-(dimethylamino)propyl]-3-ethyl carbodiimide and 20 mM N-hydroxysuccinimide in 300 ml of 0.1 M phosphate buffer (pH 6), so as to activate carboxyl groups (introduction of N-hydroxysuccinimide groups). Thus, a solid support was obtained.

Figure 2:
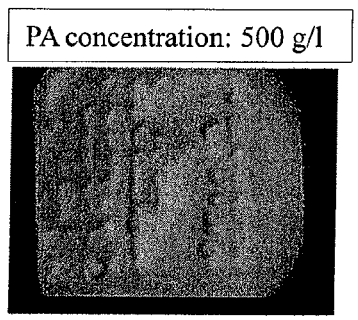
FIG. 2 shows the results of immobilizing fluorescent-labeled DNA on solid supports and photographing spot shapes using a CCD camera.
Figure 2:
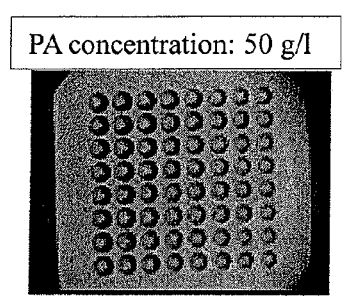
Figure 2:
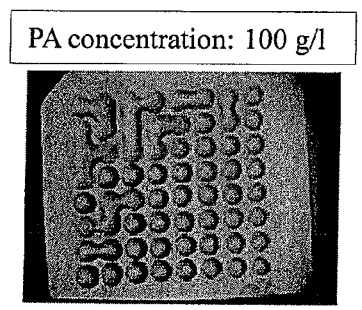
Figure 2:
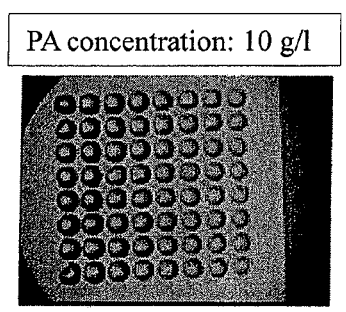
Figure 2:
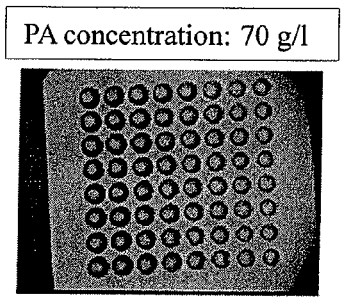
Figure 2:
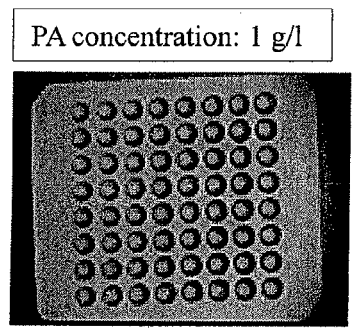

22-mer Cy3-labeled oligo DNA (5 μM) was spotted on the thus obtained solid support. The solid support was heated in an oven at 80° C. for 1 hour, washed with 2×SSC/0.2% SDS at room temperature for 15 minutes, and then at 70° C. for 5 minutes. After washing with water, centrifugal drying (1500 rpm×1 minute) was performed, so that fluorescent-labeled DNA was immobilized on the solid support. Spot shapes were photographed using a CCD camera (×20) (FIG. 2). Also, fluorescence intensity was measured using FLA-8000 (Fujifilm Holdings Corporation). The results are shown in Table 3 below.

TABLE 3

| Concentration of polyacrylic acid (g/l) | Peak intensity ratio (COO(H)/C—C) | Signal intensity | Spot shape | Appearance |
|---|---|---|---|---|
| 1 | 0.054 | 43776 | ○ | No stain |
| 10 | 0.136 | 45104 | ○ | No stain |
| 50 | 0.157 | 48408 | ○ | No stain |
| 70 | 0.173 | 48408 | ○ | No stain |
| 100 | 0.226 | 48584 | Δ | Stains |
| 500 | 0.242 | 48875 | × | Many stains |

It was demonstrated by the above results that a solid support obtained by active esterification of carboxyl groups of a substrate for which the ratio of COO peak intensity to C—C peak intensity for the C1s spectrum ranges from 0.10:1 to 0.20:1 demonstrates strong signal intensity after immobilization of labeled nucleic acids, high capacity to immobilize nucleic acids, uniform, favorable spot shapes, and favorable appearance.

All publications, patents, and patent applications cited herein are incorporated herein by reference in their entirety.

The invention claimed is:

1. A nucleic-acid-immobilized solid support for immobilizing a nucleic acid, prepared by active esterification of a carboxyl group of a substrate having a base material, an electrostatic layer formed on the base material to electrostatically attract a nucleic acid, and a carboxyl group formed on the electrostatic layer, wherein the ratio, (COO peak intensity)/(C—C peak intensity), in the C1s spectra obtained by X-ray photoelectron spectrometry (XPS) performed upon the surface of the substrate ranges from 0.10 to 0.20; and wherein a nucleic acid solution is spotted on the solid support to make a plurality of independent spots having said nucleic-acids.

2. The solid support according to claim 1, comprising a N-hydroxysuccinimide group that is formed by active esterification of a carboxyl group.

3. The solid support according to claim 1 wherein the electrostatic layer is formed by plasma-treating the base material in an ammonia gas atmosphere.

4. The solid support according to claim 1, wherein the base material comprises a carbon layer on the surface of the base material and an electrostatic layer on the carbon layer.

5. The solid support according to claim 1, wherein the independent spots are circular.

6. A nucleic-acid-immobilized solid support, which is obtained by the steps of
   (a) treating a base material with an amino-group-containing compound, wherein an electrostatic layer for electrostatically attracting a nucleic acid is formed,
   (b) contacting the electrostatic layer with a polyvalent carboxylic acid solution having a concentration ranging from 10 g/l to 70 g/l, to introduce a carboxyl group, wherein the ratio, (COO peak intensity)/(C—C peak intensity), in the C1s spectra obtained by X-ray photoelectron spectrometry (XPS) performed upon the surface of the substrate ranges from 0.10 to 0.20;
   (c) activating the carboxyl group to form an active ester group; and
   (d) spotting nucleic-acids on the electrostatic layer having the active ester group, wherein a plurality of independent spots having nucleic-acids are formed.

7. The solid support according to claim 6, wherein the active ester group is an N-hydroxysuccinimide group.

8. The solid support according to claim 6, wherein the polyvalent carboxylic acid is polyacrylic acid.

9. The solid support according to claim 6, wherein the base material is plasma-treated in an ammonia gas atmosphere to form the electrostatic layer.

10. The solid support according to claim 6, wherein the independent spots are circular.

* * * * *